(12) United States Patent
Weiss et al.

(10) Patent No.: US 9,285,360 B2
(45) Date of Patent: Mar. 15, 2016

(54) SILYLATED BIOMOLECULES

(75) Inventors: Pierre Weiss, Nantes (FR); Jerome Guicheux, Nantes (FR); Gildas Rethore, Nantes (FR); Emile Rederstorff, Nantes (FR); Samia Laib, Nantes (FR)

(73) Assignees: Institut National de la Sante et de la Recherche Medicale (INSERM), Paris (FR); Universite de Nantes, Nantes (FR); CHU Nantes, Nantes (FR); Institut Francais de Recherche pour l'Exploitation De la Mer—IFREMER, Issy les Moulineaux (FR)

( * ) Notice: Subject to any disclaimer, the term of this patent is extended or adjusted under 35 U.S.C. 154(b) by 547 days.

(21) Appl. No.: 13/574,970

(22) PCT Filed: Jan. 25, 2011

(86) PCT No.: PCT/EP2011/050981
§ 371 (c)(1),
(2), (4) Date: Sep. 19, 2012

(87) PCT Pub. No.: WO2011/089267
PCT Pub. Date: Jul. 28, 2011

(65) Prior Publication Data
US 2013/0004460 A1  Jan. 3, 2013

(30) Foreign Application Priority Data
Jan. 25, 2010  (EP) ..................... 10305079

(51) Int. Cl.
| | |
|---|---|
| *C07F 7/18* | (2006.01) |
| *G01N 33/543* | (2006.01) |
| *A61K 9/06* | (2006.01) |
| *A61K 47/36* | (2006.01) |
| *C08B 15/05* | (2006.01) |
| *C08B 37/08* | (2006.01) |
| *C08B 37/00* | (2006.01) |
| *C08G 18/10* | (2006.01) |
| *C08G 18/12* | (2006.01) |
| *C08G 18/64* | (2006.01) |
| *C08G 18/71* | (2006.01) |
| *C08J 3/075* | (2006.01) |
| *C08J 3/24* | (2006.01) |
| *C08L 5/06* | (2006.01) |
| *C08L 5/08* | (2006.01) |
| *C08L 89/00* | (2006.01) |
| *C08L 89/06* | (2006.01) |
| *C08H 1/00* | (2006.01) |
| *C08H 1/06* | (2006.01) |
| *C08L 1/28* | (2006.01) |
| *C08L 1/08* | (2006.01) |

(52) U.S. Cl.
CPC ............ *G01N 33/54353* (2013.01); *A61K 9/06* (2013.01); *A61K 47/36* (2013.01); *C07F 7/1812* (2013.01); *C08B 15/05* (2013.01); *C08B 37/003* (2013.01); *C08B 37/0045* (2013.01); *C08B 37/0072* (2013.01); *C08G 18/10* (2013.01); *C08G 18/12* (2013.01); *C08G 18/6446* (2013.01); *C08G 18/718* (2013.01); *C08H 1/00* (2013.01); *C08H 1/06* (2013.01); *C08J 3/075* (2013.01); *C08J 3/246* (2013.01); *C08L 1/28* (2013.01); *C08L 5/06* (2013.01); *C08L 5/08* (2013.01); *C08L 89/00* (2013.01); *C08L 89/06* (2013.01); *C08G 2210/00* (2013.01); *C08J 2300/108* (2013.01); *C08J 2305/06* (2013.01); *C08J 2305/08* (2013.01); *C08L 1/08* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 2005/0287560 A1* | 12/2005 | Garimella et al. | ................. 435/6 |
| 2010/0019188 A1* | 1/2010 | Warren | ................. C07F 7/1836 252/62.51 R |

FOREIGN PATENT DOCUMENTS

| | | |
|---|---|---|
| DE | 102007038333 A1 | 2/2009 |
| EP | 0664452 A2 | 7/1995 |
| WO | 2008031108 A2 | 3/2008 |
| WO | 2008040441 A2 | 4/2008 |

OTHER PUBLICATIONS

Bourges, Xavier; Weiss, Pierre, Daculsi, Guy; Legeay, Gilbert "Synthesis and general properties of silated-hydroxypropyl methylcellulose in prospect of biomedical use" Advances in Colloid and Interface Science, 99(3),Dec. 2, 2002,pp. 215-228 (doi:10.1016/S0001-8686(02)00035-0).*

Jedlicka S S et al. "Controllable surface expression of bioactive peptides incorporated into a silica thin film matrix", Journal of Physical Chemistry, Jan. 14, 2010, pp. 342-344, vol. 114, No. 1, American Chemical Society, USA.

Jedlicka S S et al. "Surface analysis by X-ray photoelectron spectroscopy of sol-gel silica", Journal of Physical Chemistry, Oct. 11, 2007, vol. 111, No. 40, pp. 11850-11857 American Chemical Society, USA.

* cited by examiner

*Primary Examiner* — Louise W Humphrey
*Assistant Examiner* — Aaron J Kosar
(74) *Attorney, Agent, or Firm* — Whitham Curtis Christofferson & Cook, PC

(57) ABSTRACT

The invention concerns: —a silylated biomolecule having the following formula (I): —the process for the preparation of a silylated biomolecule of formula (I), —the use of a silylated biomolecule of formula (I) to functionalize the surface of a support, —a process for the preparation of a hydrogel by use of a silylated biomolecule of formula (I), the hydrogel obtainable by said process, —said hydrogel as a biological tissue substitute, —a composition comprising said hydrogel in a pharmaceutically acceptable vehicle, —said composition for the release of active principle.

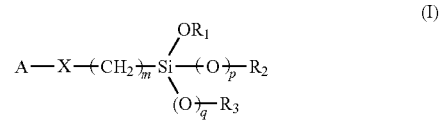

(I)

20 Claims, No Drawings

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Arg Gly Asp Ser
1

SILYLATED BIOMOLECULES

The present invention relates to a process for the silylation of biomolecules, in particular for the preparation of hydrogels.

BACKGROUND OF THE INVENTION

The development of least invasive as possible surgical techniques is a current need in regenerative medicine in order to reduce morbidity and hospitalization length of stay. In this connection, the development of new injectable matrixes is needed. These matrixes should be able to harden once implanted, to acquire the desired form and should present mechanical properties close to those of the tissue to be fixed.

Hydrogels are used in many fields, namely as tissue substitute, for example bone substitute, or for ophthalmologic surgery. The development of hydrogels presenting interesting properties in term of injectability, self-hardening and stability is therefore needed.

In this connection, Bourges et al. (Advances in Colloid and Interface Science 99, 215-228, 2002) describe the preparation of a hydrogel made from silylated hydro soluble cellulose ether (HPMC). More precisely, silylated HPMC was synthesized by reaction of HPMC with 3-glycidoxypropyltrimethoxysilane (GPTMS). A hydrogel was then prepared by introducing the silylated HPMC in a basic medium, followed by a neutralisation. However, this method is a three-step procedure (premix of HPMC and NaOH, reaction with GPTMS and quench of the reaction with acetic acid) and requires a high reaction temperature (80-100° C.).

However, cells do not adhere well to hydrogel based on silylated HPMC. Said hydrogel is therefore not suited for cells requiring adhesion for their growth. The development of new hydrogels that can be used for all kind of cells is therefore needed, in particular hydrogels based on a biomolecule different from HPMC. However, most biomolecule are temperature-sensitive, and would be destroyed or denatured by using the process based on GPTMS described above, which requires high reaction temperature. The development of other silylated biomolecule allowing the production of hydrogels is therefore required.

SUMMARY OF THE INVENTION

The present invention provides silylated biomolecule usable to prepare a hydrogel.

According to a first aspect, the invention provides a silylated biomolecule having the following formula (I):

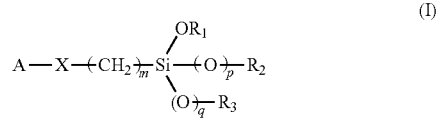

wherein:
A is a biomolecule chosen from a peptide, an oligopeptide, a protein, a deoxyribonucleic acid, a ribonucleic acid, pectin, chitosan, hyaluronic acid, and a glycolipid,
m is an integer ranging from 1 to 6,
p and q are independently 0 or 1,
X is a group chosen from —NHCONH—, —OCONH— and —CONH—, and
$R_1$, $R_2$ and $R_3$ each independently represent a $C_1$-$C_6$ alkyl group.

According to a second aspect, the invention relates to the process for the preparation of said silylated biomolecule.

According to a third aspect, the invention concerns the use of a silylated biomolecule to functionalize the surface of a support.

According to a forth aspect, the invention concerns a process for the preparation of a hydrogel comprising the steps of:
a) contacting a silylated biomolecule according to the invention with a base or an acid in an aqueous medium;
b) adjusting the pH of the aqueous medium of step a) to a pH of between 3.5 and 12.4, and optionally recovering the hydrogel.

According to a fifth aspect, the invention relates to the hydrogel obtainable by the process as described above.

According to a sixth aspect, the invention concerns the hydrogel as a biological tissue substitute.

According to a seventh aspect, the invention relates to a composition comprising a hydrogel as described above in a pharmaceutically acceptable vehicle.

According to an eighth aspect, the invention concerns said composition for the release of active principle.

DETAILED DESCRIPTION OF THE INVENTION

These and other objects, features and advantages of the invention will be disclosed in the following detailed description.

As used above, and throughout the description of the invention, the following terms, unless otherwise indicated, shall be understood to have the following meanings:

As used herein, the term "silylation" means introduction of a silyl function into said biomolecule, more precisely an alkoxysilane function.

As used herein, and except if defined otherwise, the term "biomolecule" means any organic molecule that is produced by a living organism or that is a derivative thereof, including large polymeric molecules such as proteins (natural or synthetic), polysaccharides (natural or synthetic), and nucleic acids as well as small molecules such as primary metabolites, secondary metabolites, and natural products. As examples of biomolecules, mention may be made of:
  lipid derivatives such as phospholipids, glycolipids and sterols,
  chemical messengers such as hormones and neurotransmitters,
  vitamins,
  sugar derivatives such as carbohydrate, disaccharide, oligosaccharides, polysaccharides (including cellulose),
  amino acid derivatives such as amino acids (natural and/or non-standard), peptides, oligopeptides, polypeptides, proteins (said peptides, oligopeptides, polypeptides and proteins containing natural and/or non-standard aminoacid),
  nucleotides derivatives such as nucleotides, and biological polymers such as deoxyribonucleic acid (DNA), ribonucleic acid (RNA),
  biopolymers such as lignin, proteins, DNA, RNA, oligosaccharides, polysaccharides.
  Preferably, the biomolecule is a polysaccharide, a protein, or a peptide.

As used herein, the term "polysaccharide" means a polymer made up of many monosaccharides joined together by glycosidic bonds. Natural and synthetic polysaccharides are included. Examples of polysaccharide are cellulose, hydroxypropylmethylcellulose (HPMC), hydroxyethylcellulose (HEC), carboxymethylcellulose (CMC), pectin, chitosan, hyaluronic acid.

As used herein, the term "protein" means a polymer made of amino acids arranged in a linear chain and joined together by peptide bonds between the carboxyl and amino groups of adjacent amino acid residues. Glycoprotein as well as proteins containing natural and/or non-standard aminoacid are included. Albumin, laminin, gelatin, fibronectin, vitronectin and collagen are examples of protein.

As used herein, the term "peptide" means also a polymer made of amino acids arranged in a linear chain and joined together by peptide bonds between the carboxyl and amino groups of adjacent amino acid residues. Peptides containing natural and/or non-standard aminoacid are included. Generally, peptides contain less than 50 aminoacids whereas proteins contain more than 50. RGDS (Arg-Gly-Asp-Ser; SEQ ID NO:1) is an example of peptide which can be used as a biomolecule in the present invention.

As used herein, an alkyl is a branched or linear saturated hydrocarbon chain having from 1 to 6 carbon atoms, preferably from 1 to 4 carbon atoms.

As used herein, the term <<hydrogel>> means a network of polymer chains that are water-insoluble, in which water is the dispersion medium.

As used herein, the expression "aqueous medium" means a medium wherein water is the major solvent.

According to a first aspect, the invention provides a silylated biomolecule having the following formula (I):

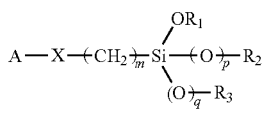
(I)

wherein:
A is a biomolecule chosen from a peptide, an oligopeptide, a protein, a deoxyribonucleic acid, a ribonucleic acid, pectin, chitosan, hyaluronic acid, and a glycolipid,
m is an integer ranging from 1 to 6,
p and q are independently 0 or 1,
X is a group chosen from —NHCONH—, —OCONH— and —CONH—, and
$R_1$, $R_2$ and $R_3$ each independently represent a $C_1$-$C_6$ alkyl group.

In an embodiment, A in the silylated biomolecule is chosen from a peptide, an oligopeptide, a protein, a deoxyribonucleic acid, a ribonucleic acid, pectin, hyaluronic acid, and a glycolipid. These biomolecules are indeed temperature-sensitive.

In a preferred embodiment, A in the silylated biomolecule is chosen from the group hyaluronic acid, pectin, collagen, gelatin, RGDS (SEQ ID NO:1) and chitosan.

According to a second aspect, the invention provides a process for the preparation of a silylated biomolecule as described above. Two processes are described therein, depending on whether the biomolecule used as starting material is carrying an amine or an alcohol function on the one hand (process 1), or a carboxylic acid function on the other hand (process 2).

The invention provides a process 1 for the preparation of a silylated biomolecule of formula (I) as described above, comprising the step of reacting a biomolecule carrying an alcohol or amine function, preferably chosen from a peptide, an oligopeptide, a protein, a deoxyribonucleic acid, a ribonucleic acid, pectin, chitosan, hyaluronic acid, a glycolipid with a silylation agent having the following formula (II):

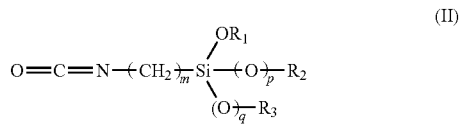
(II)

wherein:
m is an integer ranging from 1 to 6,
p and q are independently 0 or 1, and
$R_1$, $R_2$ and $R_3$ each independently represent a $C_1$-$C_6$ alkyl group.

Silylated biomolecules of formula (I), wherein X is a —NHCONH— or a —OCONH— moiety, are obtained by process 1. During the process, the amine or the alcohol function of the biomolecule reacts with the isocyanate function of the silylation agent of formula (II), leading to the formation of an urea bond (—NHCONH—) (if the biomolecule is carrying an amine function) or a carbamate bond (—OCONH—) (if the biomolecule is carrying an alcohol function) according to the following scheme:

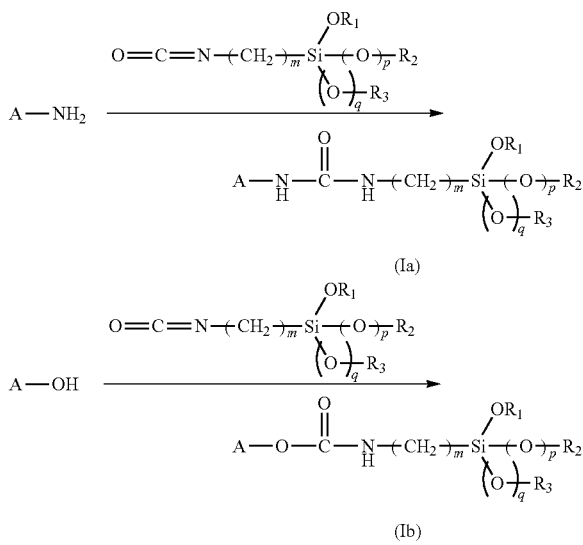

In one embodiment of process 1, the biomolecule is carrying an alcohol function and is preferably chosen from a deoxyribonucleic acid, a ribonucleic acid, pectin, chitosan, hyaluronic acid, a glycolipid and optionally from a peptide, an oligopeptide, a protein, when said peptide, oligopeptide, or protein comprise a moiety (an amino acid for example) carrying an alcohol function, for example the RGDS (SEQ ID NO:1).

In one other embodiment of process 1, the biomolecule is carrying an amine function and is preferably chosen from a peptide, an oligopeptide, a protein, a deoxyribonucleic acid, a ribonucleic acid and chitosan. The biomolecule used in the process can also carry both an alcohol function and an amine function, for example when the biomolecule is chitosan.

In a preferred embodiment of process 1, the silylation agent used in the process is 3-isocyanatopropyltriethoxysilane.

Preferably, when the biomolecule is carrying amine functions, part of said amine functions are not protonated in the reaction medium. The lone pair of the amine has indeed to be available to attack the isocyanate function.

The temperature of the reaction of process 1 is not critical and may vary in wide range. The reaction is generally carried out at a temperature from −15° C. to 40° C., preferably 0° C. to 30° C., more preferably from 15° C. to 25° C., which is advantageous as no denaturation of biomolecule occurs. Preferably, process 1 is carried out under inert atmosphere, for example under argon or nitrogen.

The reaction time is usually lasts from one hour to one week, preferably from twelve hours to five days, more preferably from one to three days.

Process 1 is generally carried out in a solvent. There is no particular restriction on the nature of the solvent to be used, provided that it has no adverse effect on the reaction or on the reagents involved. Organic solvents or mixture of organic solvent with an aqueous solution, typically water, are preferred. Examples of suitable organic solvents include acetonitrile, acetone, dimethylformamide and dimethylsulfoxide.

In one embodiment, process 1 is carried out in an anhydrous solvent, such as anhydrous acetonitrile, anhydrous acetone, anhydrous dimethylformamide or anhydrous dimethylsulfoxide, and in the presence of a base, preferably an organic base, usually an organic base containing a nitrogen atom which can be protonated, for example triethylamine, pyridine or trimethylamine.

In one other embodiment, process 1 is carried out in a mixture comprising an aqueous solution and a solvent miscible in water, such as acetonitrile, acetone, dimethylformamide and dimethylsulfoxide. The mixture is preferably a mixture of water and of dimethylsulfoxide. No base is required for this embodiment.

A second process is described therein, when the biomolecule used as starting material is carrying a carboxylic acid or a carboxylate function (process 2). Thus, the invention provides a process for the preparation of a silylated biomolecule of formula (I) as defined above, comprising the steps consisting of:

a) reacting a biomolecule carrying a carboxylic acid or a carboxylate function, preferably chosen from a peptide, an oligopeptide, a protein, pectin, hyaluronic acid, with 1-ethyl-3-(3-dimethylaminopropyl)carbodiimide hydrochloride (EDC.HCl) or with 1,1'-carbonyldiimidazole (CDI), then b) adding to the reaction medium obtained in step a) a silylation agent having the following formula (III):

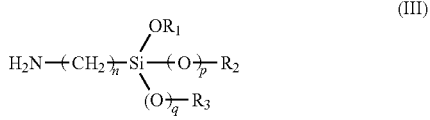

(III)

wherein,
  n is an integer ranging from 1 to 6
  p and q are independently 0 or 1, and
  $R_1$, $R_2$ and $R_3$ each independently represent a $C_1$-$C_6$ alkyl group.

Silylated biomolecules of formula (I), wherein X is a —CONH— moiety, are obtained by process 2. During process 2, the carboxylic function of the biomolecule is activated with EDC.HCl in step a) and then reacts with the amine function of the silylation agent of formula (III), leading to the formation of an amide bond (—CONH—) according to the following scheme:

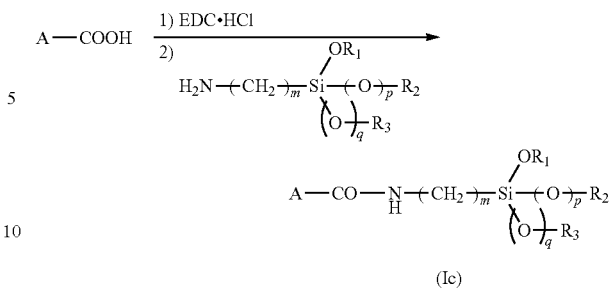

(Ic)

Preferred biomolecule used as starting material in step a) of process 2 are a peptide, an oligopeptide, a protein, pectin, and hyaluronic acid.

Step a) of process 2 can be carried out in the presence of a catalyst, such as N-hydroxysuccinimide.

The silylation agent used in step b) of process 2 is preferably (3-aminopropyl)triethoxysilane.

When EDC.HCl is used, steps a) and b) of process 2 are generally carried out in an aqueous solution, the pH of which is preferably from 4 to 6, most preferably from 4.7 to 5.3, preferably in water. When CDI is used, steps a) and b) of process 2 are generally carried out in dichloromethane or acetonitrile.

Steps a) and b) of process 2 are generally carried out at a temperature from −15° C. to 40° C., preferably 0° C. to 30° C., more preferably from 15° C. to 25° C., which is advantageous as no denaturation of biomolecule occurs.

Step a) of process 2 usually lasts from 4 h to 24 h, preferably from 12 h to 18 h, and step b) of process 2 usually lasts from 4 h to 24 h, preferably from 12 h to 18 h.

Both processes 1 and 2 lead to the formation of a strong covalent bond between the silylation agent and the biomolecule.

The weight concentration of the biomolecule used as starting material in the solvent in processes 1 and 2 is generally from 0.01 to 30%, preferably from 0.1 to 20%, more preferably from 0.5 to 15%.

Advantageously, processes 1 and 2 are carried out without any metal catalyst, more particularly tin based catalyst.

When process 2 wherein EDC.HCl is used is carried out, the reaction medium is generally homogeneous. When process 1 or process 2 wherein CDI is used are carried out, the reaction medium is generally heterogeneous. A suspension of the biomolecule in the solvent is generally observed, which can be isolated easily from the reaction mixture, for example by sedimentation or centrifugation.

According to a third aspect, the invention concerns the use of said silylated biomolecule to functionalize the surface of a support.

The alkoxysilane functions $OR_1$, $OR_2$ and $OR_3$ of the silylated biomolecule can advantageously be used to anchor the silylated biomolecule to the surface of a support. The surface can be any surface of a support able to react with an alkoxysilane function, for example a metal surface such as titanium surface or a glass surface.

According to a forth aspect, the invention concerns a process for the preparation of a hydrogel comprising the steps of:
a) contacting a silylated biomolecule according to the invention with a base or an acid in an aqueous medium;
b) adjusting the pH of the aqueous medium of step a) to a pH of between 3.5 and 12.4, and optionally recovering the hydrogel.

The aqueous medium of step a) comprises an aqueous solution and the silylated biomolecule, which can be soluble or not in the aqueous solution.

Two embodiments are possible for step a), depending if a base or an acid is used.

When the silylated biomolecule is contacted with a base in an aqueous medium during step a), the alkoxysilane function of the silylated biomolecule is hydrolyzed into a silanolate function. Adjusting the pH of the mixture thus obtained leads to protonation of the silanolate function to give silanol function, which will inherently react with another silanol function, leading to the condensation of the silylated biomolecules via the formation of —Si—O—Si— covalent bond, and hence to the formation of the hydrogel. Preferably, an inorganic base is used in step a), more preferably an alkaline or alkaline earth metal hydroxide, such as potassium or sodium hydroxide. In one embodiment of the process, the pH of the aqueous medium during step a) is from 12 to 14, preferably from 12.3 to 12.9

According to a second embodiment, the silylated biomolecule is contacted with an acid in an aqueous medium during step a), typically in an aqueous medium the pH of which is from 1 to 3, preferably around 2, for example in a HCl solution or a HEPES solution. In these conditions, the alkoxysilane function of the silylated biomolecule is hydrolyzed into a silanol function, which will inherently react with another silanol function, leading to the condensation of the silylated biomolecules via the formation of —Si—O—Si— covalent bond, and hence to the formation of the hydrogel. This embodiment is particularly suited for silylated biomolecule, wherein the biomolecule is a peptide, an oligopeptide, a protein, or hyaluronic acid.

The process for the preparation of a hydrogel is advantageously based on auto-condensation of silanol functions just by adjusting the pH, without requiring toxic additives to be added.

The following embodiments are preferred to carry out step a) of the process for the preparation of a hydrogel.

Generally, step a) lasts from 10 minutes to three days, preferably from 1 hour to 36 hours, more preferably from 12 hours to 24 hours. Usually, step a) is carried out until a homogeneous reaction medium is obtained.

In an embodiment, in step a), the silylated biomolecule and the base or the acid are further contacted with a second silylated biomolecule of different nature. Condensation occurs between two silylated biomolecules of different nature, leading to a hydrogel comprising two different biomolecules. Said second silylated biomolecule generally carries an alkoxysilane function. Said second silylated biomolecule typically has the following formula (IV):

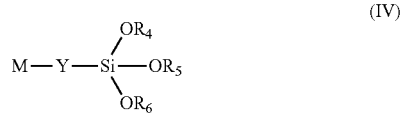

wherein:
M is a biomolecule,
Y is a linker group between the biomolecule and the silane,
$R_4$, $R_5$ and $R_6$ each independently represent a $C_1$-$C_6$ alkyl group.

The second silylated biomolecule is preferably a silylated polysaccharide, in particular a silylated cellulose derivative, such as silylated cellulose, silylated hydroxyethylcellulose (HEC) or silylated HPMC.

The proportion of the two silylated biomolecules can vary to a large extent, for example 100 parts by weight of a first silylated biomolecule can be used for 1 part by weight of a second silylated biomolecule in step a), or the same weight for both silylated biomolecules can be used. By varying the proportions and the nature of the two silylated biomolecules, the structure and nature of the hydrogel can easily be changed and adapted depending on which further use of the hydrogel is searched for, and which biophysical, biological, physical and chemical properties are required for that use.

In an embodiment, in step a), the silylated biomolecule is a silylated peptide or a silylated protein and the second silylated biomolecule is based on any biomolecule. In a preferred embodiment, the silylated biomolecule is a silylated peptide or a silylated protein and the second silylated biomolecule is a silylated polysaccharide, in particular a silylated cellulose derivative, such as silylated cellulose or silylated HPMC.

In preferred embodiments, step a) comprises contacting:
silylated collagen with silylated HPMC (as second silylated biomolecule) (leading to a hydrogel containing HPMC and collagen),
silylated hyaluronic acid with silylated HPMC (as second silylated biomolecule) (leading to a hydrogel containing HPMC and hyaluronic acid),
silylated RGDS (SEQ ID NO:1) with silylated HPMC (as second silylated biomolecule) (leading to a hydrogel containing HPMC and RGDS (SEQ ID NO:1)),
silylated pectin with silylated hyaluronic acid (as second silylated biomolecule) (leading to a hydrogel containing pectin and hyaluronic acid).

In one embodiment, the second silylated biomolecule has been prepared according to process 1 or 2, wherein the biomolecule of the second silylated biomolecule is of any nature (for example, silylated HPMC can be the second silylated biomolecule, although the procedure of process 1 or 2 is followed).

In one other embodiment, the second silylated biomolecule has not been prepared according to the processes according to the invention. For example, the second silylated biomolecule has been prepared from 3-glycidoxypropyltrimethoxysilane (GPTMS), as described in Bourges et al. Advances in Colloid and Interface Science 99, 215-228, 2002, and the second silylated biomolecule has the following formula (V):

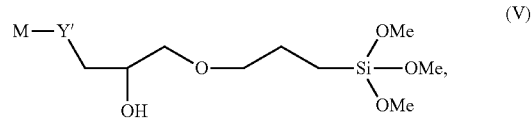

wherein M is a biomolecule and Y' is —O—, —NH— or —(CO)O—. Before reaction with GPTMS, when the biomolecule was carrying an alcohol, an amine or a carboxylic acid function, Y' is respectively —O—, —NH— or —(CO)O—.

In an embodiment, in step a) the silylated biomolecule and the base are further contacted with two or more other silylated biomolecules of different nature. A hydrogel comprising at least three biomolecules is thus obtained.

The following embodiments are preferred to carry out step b) of the process for the preparation of a hydrogel.

Step b) usually lasts from 1 min to 3 days, preferably from 20 min to 24 hours. Generally, step b) is carried out until the reaction medium is unable to flow. Rheological experiments can be carried out to determine exactly the gelling time.

Preferably, a buffering agent or an isotonic solution is added during step b), for example 4-(2-hydroxyethyl)-1-piperazineethanesulfonic acid (HEPES). The use of buffering agent or the isotonic solution leads to a reaction medium the pH of which is around 7.4, i.e. physiological pH.

In an embodiment, in step b), the pH of the aqueous medium is adjusted to a pH of between 4 and 11, preferably 5 to 10, more preferably 6 to 8, more preferably from 7 to 7.4.

Moreover, before gelation occurs and as long as the medium is able to flow (usually in the first hour of step b)), cells can be incorporated in the medium. Thus, in one embodiment of the process, cells are added during step b). An hydrogel advantageously comprising cells can be obtained.

Before gelation occurs and as long as the medium is able to flow, an active principle can also be incorporated in the medium. Thus, in one embodiment of the process, an active principle is added during step b). A hydrogel advantageously comprising an active principle can be obtained, which will be able to release said active principle.

Preferably, steps a) and b) of the process for the preparation of a hydrogel are carried out in sterile conditions, in particular when the further intended use of the hydrogel is for in vivo or in vitro applications, in particular in vivo applications.

According to a fifth aspect, the invention relates to the hydrogel obtainable by the process as described above.

The biophysical, biological, physical and chemical properties of the hydrogel can advantageously be modulated by varying the proportion and the nature of the silylated biomolecule comprised therein.

Generally, the hydrogel can advantageously be easily injected through syringes.

Generally, the hydrogel is self-hardening. Preferably, the hydrogel crosslinks by itself at physiological pH, and can therefore be used in tissue engineering.

With a judicious choice of the biomolecule on which the hydrogel is based, the hydrogel is also biodegradable, in particular by enzymatic methods. For example, a hydrogel containing hyaluronic acid is degradable by hyaluronidase, and a hydrogel containing collagen is degradable by collagenase.

Usually, the hydrogel obtained promotes cell adhesion. Hydrogels containing HPMC and another biomolecule promote better cell adhesion than HPMC-based hydrogel.

The hydrogel containing two different biomolecules are particularly preferred. The preferred hydrogel are the one comprising the following biomolecules association:
  HPMC and collagen,
  HPMC and hyaluronic acid,
  HPMC and RGDS (SEQ ID NO:1)
  pectin and hyaluronic acid.

According to a sixth aspect, the invention concerns the hydrogel as a biological tissue substitute, for example as cartilage-like tissue substitute, bone substitute, heart tissue or skin substitute The hydrogel for its use as a biological tissue substitute, the use of the hydrogel for the preparation of a tissue substitute, and the therapeutic treatment method comprising the use of the hydrogel as tissue substitute are also subject matters of the present invention.

According to a seventh aspect, the invention relates to a composition comprising a hydrogel as described above in combination with a pharmaceutically acceptable vehicle. The composition may also further comprise an active principle.

According to an eighth aspect, the invention concerns the use of said composition for the release of an active principle. The composition for its use for the release of active principle, the use of the composition for the preparation of drug releasing an active principle, and the therapeutic treatment method comprising the use of the release of active principle to release active principles, are also subject matters of the present invention.

EXAMPLES

Abbreviations
HPMC-Si: silylated HPMC
Coll-Si: silylated collagen
HA-Si: silylated hyaluronic acid
Pec-Si: silylated pectine
HBSS: Hank's Buffered Salt Solution
C: collagenase
H: hyaluronidase Example 1

Silanization Protocol in Anhydrous and Heterogeneous Conditions (Process 1)

The desired lyophilized polyose, protein or peptide was suspended into anhydrous acetonitrile at a total weight ratio of 10-15%, 3-4%, and 0.5-1.5% respectively. At least one equivalent of triethylamine per function to modify (OH or $NH_2$) was added to the suspension. A mechanical stirring and a nitrogen (or argon) bubbling was applied for at least 20 min before the addition of the silylated reagent, which might contain at least one alkoxysilane group and one isocyanate function (for example 3-isocyanatopropyltriethoxysilane). The circulation of inert gas and the stirring were maintained at ambient temperature (20-25° C.) for several days, depending on the amount of the starting materials (e.g. 3 days for 8 g of biomolecule). After sedimentation or centrifugation, the supernatant was removed and the residual solid or paste was washed at least 3 times with a large amount of pure ethanol, and then dried at ambient temperature or under vacuum. The solid can also be collected and washed by filtration on a nylon membrane of 0.2 µm.

The presence of the alkoxysilane group onto the modified macromolecule was detected by solid state NMR MAS $^{29}Si$ (2.5 kHz at 500 Mhz).

Example 2

Preparation of Hydrogels

Step 1: Preparation of the Basic Solution
  Method A: one or more of the desired silylated compounds obtained by the procedure described above was poured into a 0.2 M sodium hydroxide solution at a total weight percentage of 1 to 6. After one night of mechanical stirring, the resulting viscous solution or suspension was transferred into a regenerated cellulosic dialysis tubing of MWCO 6-8000 previously rinsed with a 0.09 M sodium hydroxide solution. The basic solution/suspension was washed with 19 volumes of a 0.09 M sodium hydroxide solution for 18 hours, and then with 20 volumes of a new 0.09 M sodium hydroxide solution for 2 hours. The final pH of the silylated macromolecule solutions was 12.4. Also, one or more of these solutions can be mixed together at various ratios. A classical example was to mix 3 volumes of a 3 wt % silylated biomolecule solution with 1 volume of a 1 to 6 wt % second silylated biomolecule solution.
  Method B: The second and additionals silylated compounds were directly added on the solid state into a basic macromolecule solution prepared as above (typically 10-40 mg of a second silylated macrobiomolecule per ml of a 3 wt % silylated biomolecule solution).

The basic solution can be sterilized under 254 nm UV irradiation for 15 min.

Step 2: Addition of the Acidic Buffer
  0.5 volume of steam sterilized 4-(2-hydroxyethyl)piperazine-1-ethanesulfonic acid (HEPES) of pH 3.6 was added to the desired basic solution prepared in step 1.

The mixture was homogeneized by using luer-lock syringes and luer-lock connectors. The final pH of the hydrogels was 7.4, and the gelation time varied between 10 min and 24 h.

The viscoelastic properties of the hydrogels were evaluated by rheological measurements.

Example 3

Enzymatic Degradation Assays of Hydrogels Prepared from Silylated Biomolecules all Obtained by the Process According to the Invention To 1.5 ml of hydrogel prepared as above is added either 1.5 ml of HBSS (Hank's Buffered Salt Solution) alone, either 1.5 ml of HBSS containing 3 mg of collagenase, either 1.5 ml of HBSS containing 1.5 mg of hyaluronidase. The mixtures were incubated at 37° C.

The following table shows if a degradation is obtained by adding collagenase (C) or hyaluronidase (H) to the hydrogel.

| Nature of the hydrogel | HPMC—Si 3 wt % + Coll—Si 1 wt % (3:1) + HEPES | HPMC—Si 3 wt % + HA—Si 6 wt % (3:1) + HEPES | HPMC—Si 3 wt % + Pec—Si 4 wt % (3:1) + HEPES | Pec—Si 4 wt % + HA—Si 6 wt % (3:1) + HEPES | Pec—Si 4 wt % + HEPES |
|---|---|---|---|---|---|
| Solution added | C | H | H | H | H |
| Enzymatic degradation | yes | yes | yes | yes | yes |

Example 4

Enzymatic Degradation Assays of Hydrogels Prepared from One Silylated Biomolecule Obtained by a Process According to the Literature, and Optionally from Another Silylated Biomolecule Obtained by the Process According to the Invention Examples of hydrogels made with the silylated HPMC obtained by an antecedent silanization protocol (see Bourges et al. (Advances in Colloid and Interface Science 99, 215-228, 2002) which was basically as followed: heptane/1-propanol, NaOH pellets, 3-glycidoxypropyltrimethoxysilane, heating at 80° C. for 3 hours, quenching with frozen acetic acid, washing with water/acetone, and lyophilisation. Coll-Si, HA-Si and Pec-Si were obtained by the process according to the invention as illustrated in example 1.

The following table shows if a degradation is obtained by adding collagenase (C) or hyaluronidase (H) to the hydrogel.

| Nature of the hydrogel | HPMC—Si 3 wt % + HEPES (comparative example) | HPMC—Si 3 wt % + HEPES (comparative example) | HPMC—Si 3 wt % + Coll—Si 1 wt % (3:1) + HEPES | HPMC—Si 3 wt % + HA—Si 6 wt % (3:1) + HEPES | HPMC—Si 3 wt % + Pec—Si 4 wt % (3:1) + HEPES |
|---|---|---|---|---|---|
| Solution added | C | H | C | H | H |
| Enzymatic degradation | no | no | yes | yes | yes |

Examples 3 and 4 show that the presence of biomolecules such as collagen, hyaluronic acid, or pectine ($\alpha$ 1-4 glycosidic link) within the HPMC ($\beta$1-4 glycosidic link) based hydrogels induces enzymatic degradation properties.

Example 5

In Vitro Assays—Cells Morphology and Adhesion

Example of Protocol for 2D Culture:

The hydrogels were prepared as described previously, and before their gelation time was reached, 0.3 ml of each mixture was directly poured into a well of a 24-multi wells plate with ultra-low attachment surface. Once the hydrogels were well reticulated, 0.5 ml of classical culture medium was added per well and left over at least a night so it can diffuse within the hydrogel. In each well the culture medium was then replaced by 0.5 ml of culture medium containing about 20.000 cells (e.g. MC3T3). The cells morphology and viability were evaluated by "live&dead" assays and optical microcopy analysis (alive cells in green and dead cells in red). The culture medium was changed every 2 days and the observations occurred generally at 5 h, 24 h, 48 h, 7 days and sometimes more.

No cell adhesion was observed onto the silylated HPMC hydrogel, whatever is the silanization protocole, the one from Bourges et al. (Advances in Colloid and Interface Science 99, 215-228, 2002) or the one according to the invention. Although the HPMC-Si obtained with the two different processes present different physico-chemical properties, their biological response is alike.

But when this hydrogel is mixed with some silylated collagen or hyaluronic acid, the cells tended to stretch and to stick to the hydrogel surface after the renewal of the culture medium. Contrary to the silylated HPMC hydrogel, the silylated pectine favorized the cell adhesion, and when combined with some silylated hyaluronic acid, this property seemed to increase.

Examples of Protocol for 3D Culture:

The hydrogels were prepared as described previously, and before their gelation time was reached, the amount of the hydrogel was equally divided between the 2 syringes used to make the mixture. Few μl of culture medium containing the cells were introduced into one of the syringe with a pipette. The cells were dispersed into the hydrogel by connecting the 2 syringes with a luer-lock connector. The final concentration of cells was about $1.10^6$ cells per ml of hydrogel. Once homogenized, 0.3 ml of the mixture was poured into a well of a 24 well plate, and one or two hours later, 0.5 ml of culture medium was added. The culture media was changed every two days, and the cells morphology and viability were evaluated in the same fashion than the 2D cultures.

The invention claimed is:

1. A hydrogel prepared by a process comprising the steps of:
   a) contacting a silylated biomolecule with a base or an acid, in an aqueous medium, wherein the silylated biomolecule has the following formula (I):

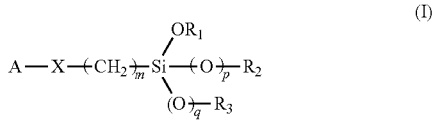

wherein:
   A is a biomolecule selected from the group consisting of a hyaluronic acid, pectin, collagen, gelatin, RGDS (SEQ ID NO:1) and chitosan,
   m is an integer ranging from 1 to 6,
   p and q are independently 0 or 1,
   X is a group chosen from —NHCONH—, —OCONH— and —CONH—, and
   $R_1$, $R_2$ and $R_3$ each independently represent a $C_1$-$C_6$ alkyl group; and
   b) adjusting the pH of the aqueous medium of comprising the silylated biomolecule of step a) to a pH of between 3.5 and 12.4;
   whereby said silylated biomolecule auto-condensates via formation of —Si—O—Si— covalent bonds.

2. The hydrogel of claim 1, wherein said process further comprises the step of recovering the hydrogel.

3. The hydrogel of claim 1 wherein in step a), said silylated biomolecule and said base or said acid are further contacted with a second silylated biomolecule of formula (IV):

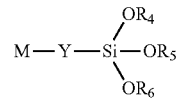

wherein:
   M is a biomolecule different from A,
   Y is a linker group between the biomolecule and the silane, and
   $R_4$, $R_5$ and $R_6$ each independently represent a $C_1$-$C_6$ alkyl group.

4. The hydrogel of claim 3, wherein M is a polysaccharide.

5. The hydrogel of claim 4, wherein said polysaccharide is cellulose, hydroxyethylcellulose or hydroxypropylmethylcellulose.

6. The hydrogel of claim 5, wherein said polysaccharide is hydroxypropylmethylcellulose.

7. The hydrogel of claim 3, wherein M is selected from the group consisting of a peptide, an oligopeptide, a protein, a deoxyribonucleic acid, a ribonucleic acid, pectin, chitosan, hyaluronic acid and a glycolipid, wherein M is different from A.

8. The hydrogel of claim 3, wherein A is pectin and M is hyaluronic acid.

9. A composition comprising the hydrogel of claim 1, and one or more cells.

10. A biological tissue substitute comprising a hydrogel prepared by a process comprising the steps of:
   a) contacting a silylated biomolecule having the following formula (I):

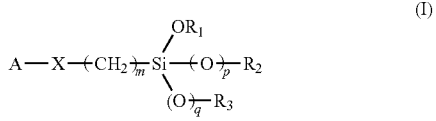

wherein:
   A is a biomolecule selected from the group consisting of a hyaluronic acid, pectin, collagen, gelatin, RGDS (SEQ ID NO:1) and chitosan,
   m is an integer ranging from 1 to 6,
   p and q are independently 0 or 1,
   X is a group chosen from —NHCONH—, —OCONH— and —CONH—, and $R_1$, $R_2$ and $R_3$ each independently represent a $C_1$-$C_6$ alkyl group; with a base or an acid in an aqueous medium; and b) adjusting the pH of the aqueous medium of step a) to a pH of between 3.5 and 12.4.

11. The biological tissue substitute of claim 10, wherein said biological tissue substitute further comprises one or more cells.

12. The biological tissue substitute of claim 11, wherein said cells require adhesion for growth.

13. The biological tissue substitute of claim 10, wherein said biological tissue substitute is a cartilage-like tissue substitute, a bone substitute, a heart tissue substitute or a skin substitute.

14. A composition comprising a biological tissue substitute according to claim 10 in combination with a pharmaceutically acceptable vehicle.

15. A process for the preparation of an hydrogel comprising the steps of:

a) contacting a silylated biomolecule with a base or an acid, in an aqueous medium, wherein the silyated biomolecule has the following formula (I):

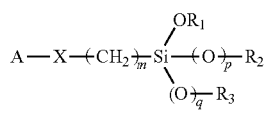
(I)

wherein:
A is a biomolecule selected from the group consisting of hyaluronic acid, pectin, collagen, gelatin, RGDS (SEQ ID NO:1) and chitosan,
m is an integer ranging from 1 to 6,
p and q are independently 0 or 1,
X is a group chosen from —NHCONH—, —OCONH— and —CONH—, and $R_1$, $R_2$ and $R_3$ each independently represent a $C_1$-$C_6$ alkyl group; and b) adjusting the pH of the aqueous medium comprising the silylated biomolecule of step a) to a pH of between 3.5 and 12.4;
whereby said silylated biomolecule auto-condensates via formation of —Si—O—Si— covalent bonds.

16. The process according to claim 15, wherein in step a), the silylated biomolecule and the base or the acid are further contacted with a second silylated biomolecule of formula (IV):

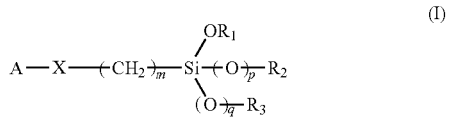
(I)

wherein:
M is a biomolecule different from A,
Y is a linker group between the biomolecule and the silane, and
$R_4$, $R_5$ and $R_6$ each independently represent a $C_1$-$C_6$ alkyl group.

17. Process according to claim 16, wherein M is a polysaccharide.

18. Process according to claim 17, wherein the polysaccharide is cellulose, hydroxyethylcellulose or hydroxypropylmethylcellulose.

19. The process according to claim 16, wherein M is selected from the group consisting of a peptide, an oligopeptide, a protein, a deoxyribonucleic acid, a ribonucleic acid, pectin, chitosan, hyaluronic acid and a glycolipid, wherein M is different from A.

20. The process of claim 15, further comprising the step of recovering the hydrogel.

* * * * *